United States Patent
Kim et al.

(10) Patent No.: US 7,824,618 B2
(45) Date of Patent: Nov. 2, 2010

(54) SENSOR STRUCTURE AND METHOD OF FABRICATING THE SAME

(75) Inventors: Yong Shin Kim, Daejeon-Shi (KR); Yun Tae Kim, Daejeon-Shi (KR); Hae Sik Yang, Daejeon-Shi (KR); Young Jun Kim, Daejeon-Shi (KR); Seung Chul Ha, Gyeonggi-Do (KR); Yoon Seok Yang, Gyeonggi-Do (KR)

(73) Assignee: Electronics and Telecommunications Research Institute, Daejeon-shi (KR)

( * ) Notice: Subject to any disclaimer, the term of this patent is extended or adjusted under 35 U.S.C. 154(b) by 1111 days.

(21) Appl. No.: 10/913,422

(22) Filed: Aug. 9, 2004

(65) Prior Publication Data

US 2005/0142034 A1 Jun. 30, 2005

(30) Foreign Application Priority Data

Dec. 26, 2003 (KR) .................... 10-2003-0097259

(51) Int. Cl.
*G01N 27/00* (2006.01)
(52) U.S. Cl. .................. 422/82.02; 422/88; 422/98; 73/23.2; 73/25.01; 73/25.05; 73/31.01; 73/31.02; 73/31.05; 73/31.03
(58) Field of Classification Search ............. 422/82.01, 422/82.02, 83, 90, 98; 73/23.2, 25.01, 25.03, 73/25.05, 31.05–31.03, 31.06
See application file for complete search history.

(56) References Cited

U.S. PATENT DOCUMENTS 6,331,244 B1 12/2001 Lewis et al.
6,440,792 B1 * 8/2002 Shiao et al. ................ 438/243
6,752,964 B1 * 6/2004 Grubbs et al. ................ 422/98
2003/0039586 A1 * 2/2003 Toyoda et al. ................ 422/98

OTHER PUBLICATIONS

Zee, Frank et al., Micromachined polymer-based chemical gas sensor array, Sensors and Actuators B: Chemical, vol. 72, Issue 2, Jan. 25, 2001, pp. 120-128.*
Lonergan, Mark C. et al., Array-Based Vapor Sensing Using Chemically Sensitive, Carbon Black-Polymer Resistors, Chemistry of Materials., vol. 8, Issue 9, Sep. 1996, pp. 2298-2312.*
Yang et al.; "Substrate Temperature Dependence of Carbon Black-Organic Polymer Composite Vapor Sensors for Vapor Characterization"; The Electrochemical Society, Inc.; 2003; 2 pages.
Haug et al.; "Chemical sensors based upon polysiloxanes: comparison between optical, quartz microbalance, calorimetric, and capacitance sensors"; Sensors & Actuators; 1993; pp. 383-391.

* cited by examiner

*Primary Examiner*—Jill Warden
*Assistant Examiner*—Cedric Chan
(74) *Attorney, Agent, or Firm*—Lowe Hauptman Ham & Berner LLP

(57) ABSTRACT

Provided is a sensor structure comprising a heater and a temperature sensor at the center of a membrane having a well structure, allowing a temperature to be rapidly controlled with low power, and the object is analyzed using a conductivity change measured at two or more substrate temperatures with a pair of detecting electrode and a detecting layer implemented on the heater, wherein the sensing layer can include a conductive particle and a non-conductive organic composite.

11 Claims, 5 Drawing Sheets

SENSOR STRUCTURE AND METHOD OF FABRICATING THE SAME

BACKGROUND

1. Field of the Invention

The present invention generally relates to a sensor structure and method of fabricating the same.

2. Discussion of Related Art

Generally, in order to check chemical species that exists in a gas state is performed using chemical analyzing instruments such as a chromatography or a mass analyzer. Recently, such chemical analysis is possible to be performed using a mobile device, so that there is an increasing demand in checking in real-time and on the spot whether or not the air is contaminated, the food quality is well managed, the virus is infected, and the chemical, biological and radiological substance is contaminated. In this respect, there has been an effort to make the existing chemical analysis device smaller.

However, such analysis instruments have a limitation so that, recently, a mobile analysis device has been progressively developed using a small chemical sensor. In particular, an electronic nose device has been progressively developed using a sensor array comprising a number of chemical sensors in order to detect various chemical species, contrary to the characteristics of the existing single sensor with which only a specific chemical species is detected.

As a sensor technology mainly used in the electronic nose system, there are a metal-oxide-semiconductor sensor represented with $SnO_2$, a quartz crystal microbalance (QCM) device using a bulk acoustic, a surface acoustic wave (SAW) device using a surface acoustic, a conducting polymer device, a polymer composite device comprising a conductive particle and a non-conductive polymer, and a colorimetric technology using an absorption wavelength change of a single molecule.

Among these various sensor technologies, the conducting polymer and the polymer composite technologies have a merit in that it is capable of making various sensors easily to fabricate the sensor array for electronic nose system. However, since such sensor materials generally show a characteristic sensitive to the temperature and moisture, there is a problem that the temperature and the moisture should remain constant.

A chemical sensor fabricated with the prior art will now be described with reference to FIG. 1.

A chemical sensor in FIG. 1 has a structure that a detecting electrode 11 and a sensing layer 12 are formed on the front side and a heater line 13 and an underlying protective layer 14 are formed on the back side.

Although a polymer composite and a conducting polymer sensors using an organic polymer can operate at room temperature, since the detecting characteristics vary according to the temperature, a constant temperature condition should be met in order to obtain the constant detecting pattern. Generally, by keeping the temperature constantly at more or less 40° C., a measurement error due to the change of the external temperature can be minimized. However, the conventional chemical sensor has a significant heat loss to the outside, so that there existed a problem that there was too much power consumption to make a very small electronic nose device requiring the temperature control.

Further, since a physiochemical interaction between the detected chemical species and the sensor material varies according to the temperature of a sensor substrate, the detecting pattern of the sensor array is also changed, and experimental parameters relevant to the interaction can be derived by the measurement of the change of the detecting response according to the temperature. (Schierbaum et al, Sensors and Actuators A, 1992, 31, 130). This result is also disclosed in the preceding research (U.S. Pat. No. 5,911,872).

However, in order to perform the temperature-dependent measurement with the conventional substrate, it take more than 10 minutes to stabilize the temperature, so that a lot of power is consumed for very small portable electronic nose device and a lot of gases are required in stabilizing the sensor to make it difficult to substantially implement.

SUMMARY OF THE INVENTION

The present invention is directed to a method for exactly determining chemical species and its concentration with using a sensor comprising organic polymer composite layer and embedded microheater with a membrane structure for minimizing a heat loss, by actively controlling a temperature and using a detecting pattern based on the temperature change.

The present invention is also directed to a method for exactly determining chemical species and their concentration by actively controlling a temperature of a sensor device with an incorporated low power microheater, and with this, by using a temperature-dependent change of a detecting pattern in a chemical sensor array comprising one or more polymer composite sensors.

Further, the present invention is directed to a method of determining the chemical species and the concentration of analyzed object with high credibility through the measurement of a detecting response based on a temperature by allowing the temperature to be rapidly controlled with low power consumption.

One aspect of the present invention is to provide a sensor structure comprising: a membrane structure having a well structure; at least one pair of detecting electrodes arranged in the well structure; a sensing layer formed on the detecting electrode and made of a conductive particle and a non-conductive polymer composite; and a heater for controlling a temperature in the well structure, wherein the analysis is performed by measuring a change of a physical quantity of the sensing layers with regard to the exposure of the chemical species at at least two temperatures using the sensing layer.

Another aspect of the present invention is to provide a method of fabricating a sensor structure comprising the steps of: forming a detecting electrode on one side of a semiconductor substrate; forming a dielectric layer that corresponds to a membrane on the one side of the semiconductor substrate; forming a heater on the membrane; etching the other side of the semiconductor substrate to make the detecting electrode exposed to form a well structure; and forming a sensing layer made of a conductive particle and a non-conductive polymer, in the well structure, wherein the analysis is performed by measuring a change of a physical quantity of the sensing layers with regard to the exposure of the chemical species at at least two temperatures using the sensing layer.

DETAILED DESCRIPTION OF PREFERRED EMBODIMENTS

Figure 1:
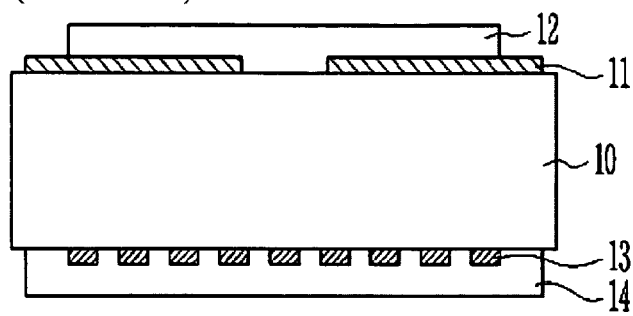
FIG. 1 is a cross sectional view of a sensor structure fabricated by the prior art.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the thickness of layers and regions are exaggerated for clarity.

Figure 2:
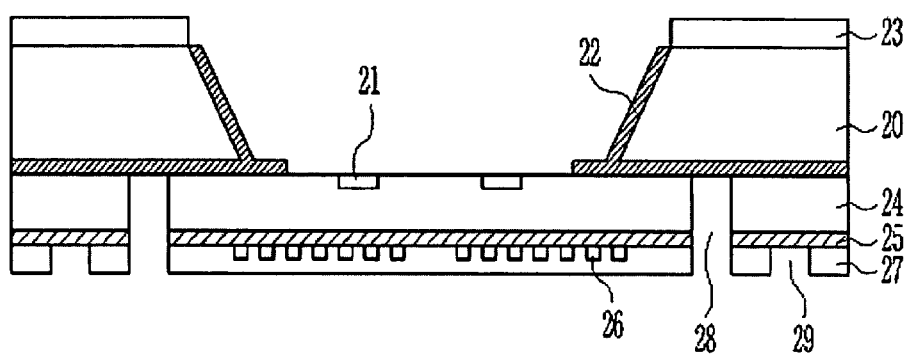
FIG. 2 is a cross sectional view of a sensor structure according to an embodiment of the present invention.

FIG. 2 is a schematic cross sectional view of a unit sensor structure in a sensor array for use in a chemical species determination method.

This sensor structure comprises a membrane structure having a well structure; at least one pair of detecting electrodes 21 arranged in the well structure; a sensing layer formed on the detecting electrode 21 and made of a conductive particle and a non-conductive polymer composite; and a heater for controlling a temperature in the well structure, wherein the analysis is performed by measuring a change of a physical quantity of the sensing layers with regard to the exposure of the chemical species at at least two temperatures using the sensing layer.

A method of fabricating a sensor array structure according to an embodiment of the present invention will now be specifically described in each step with reference to FIGS. 3A to 3G.

(Forming a Substrate Protective Layer 22)

Figure 3A:
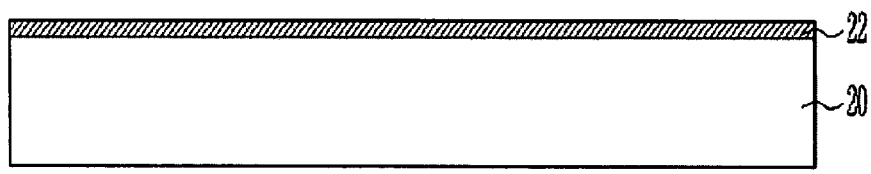
FIGS. 3A to 3G are cross sectional views showing each step of a method of fabricating a sensor array structure according to an embodiment of the present invention.

Referring to FIG. 3A, in order to make electrical isolation between a semiconductor substrate 20 and a detecting electrode 21, first, a substrate protective layer 22 is formed on one side of the semiconductor substrate 20. Preferably, the semiconductor substrate 20 is one that is both-side polished, and is generally a Si Substrate, a GaAs substrate, etc. It is desirable that the substrate protective layer 22 is an oxide layer formed to a thickness of 100 nm.

(Forming a Detecting Electrode 21)

Figure 3B:
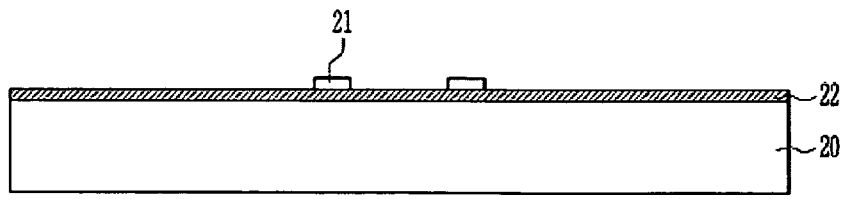

Referring to FIG. 3B, a metal material is deposited on the substrate protective layer 22 placed on one side of the semiconductor substrate 20, and then, it is patterned to form a detecting electrode shape. The detecting electrode 21 is used to detect the physical change of the sensor material. As a material for this, for example, Au, Pt, Al, Mo, Ag, TiN, W, Ru, Ir or p-Si, etc can be used. Before depositing the metal material, a material that can increase adhesion between the substrate protective layer 22 and the detecting electrode 21 can be deposited. For example, the material that can increase the adhesion is Cr or Ti. The material that increases the adhesion has a thickness of 5 nm, and it is desirable that the detecting electrode material has a thickness of more or less 100 nm. Patterning can be performed, for example, using an etching process, or alternatively, using a lift-off process.

(Removal of the Substrate Protective Layer 21 in the Detection Area)

Figure 3C:
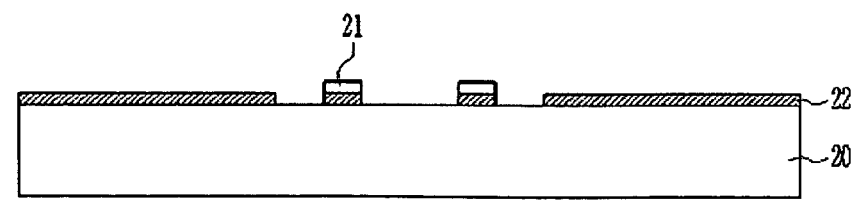

Referring to FIG. 3C, a step of removing the substrate protection layer 22 in the detecting area is required in advance. The removal of the substrate protective layer 22 can be performed using a wet etch process or a dry etch process. The reason that the substrate protective layer 22 of the detecting layer is removed is that an electrical connection between the detecting layer and the detecting electrode should be made in forming the detecting layer with a sensor solution within the formed well structure after removing the bulk silicon in the subsequent process.

(Forming a Membrane Dielectric Layer 24, a Supplementary Dielectric Layer 25 and a Microheater Heat Line 26)

Figure 3D:
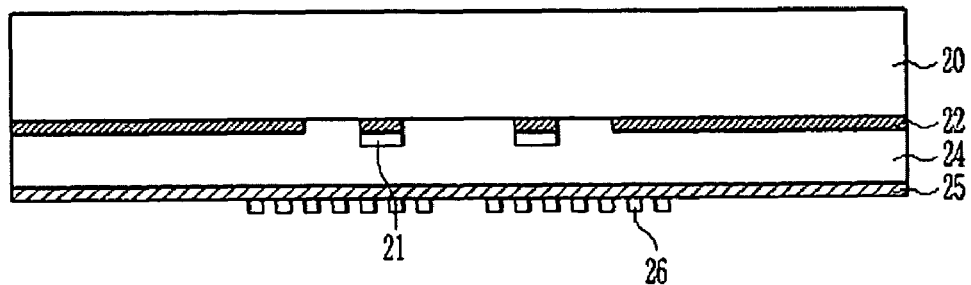

Referring to FIG. 3D, in order to exclude an electrical interference between the detecting electrode 21 and the microheater, and to form a membrane thin film that physically supports a floor in the well structure, the membrane dielectric layer 24 and the supplementary dielectric layer 25 are formed. Preferably, a 1.5 um silicon nitride layer and a 300 nm silicon oxide layer are deposited. The supplementary dielectric layer 25 serves to attenuate a stress formed by the membrane dielectric layer 24.

Next, after depositing a metal material on the supplementary dielectric layer 25, the metal material is patterned to fabricate the microheater heat line 26, for use in temperature control of the sensor material. As a material for this, there can be used Au, Pt, Al, Mo, Ag, TiN, W, Ru, Ir or p-Si, etc., for example.

Before depositing the metal material, a material that increases the adhesion between the supplementary dielectric layer 25 and the metal material can be deposited. For example, the material that increases the adhesion is Cr or Ti. The material that increases the adhesion can be formed to a thickness of 5 nm, and the metal material can be formed to a thickness of 100 nm. Patterning can be performed, for example, using an etching process, or alternatively, using a lift-off process. Preferably, the temperature sensor that can measure the temperature is fabricated simultaneously in forming the heater, and as a typical material that also serves as this, there are Pt and p-Si, etc.

(Forming the Lower Protective Layer 27 and the Upper Protective Layer 23)

Figure 3E:
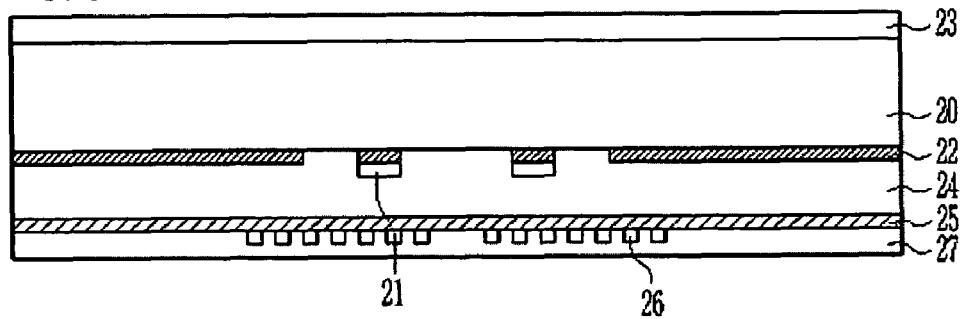

Referring to FIG. 3E, the lower protective layer 27 is formed to protect the microheater heat line 26 from the external physical attack and the electrical short circuit. As an example, it can be a silicon oxide layer, which has a thickness of 100 to 300 nm. Next, the upper protective layer 23 that can be used as a mask in silicon bulk etching is deposited and patterned. When the bulk silicon is etched by an anisotropic wet etching process, it is desirable that a more or less 500 nm thick silicon oxide layer or silicon nitride layer is employed, which is hard to be etched with an etchant.

(Opening a Detecting Electrode Pad 28 and a Heater Connection Pad 29)

Figure 3F:
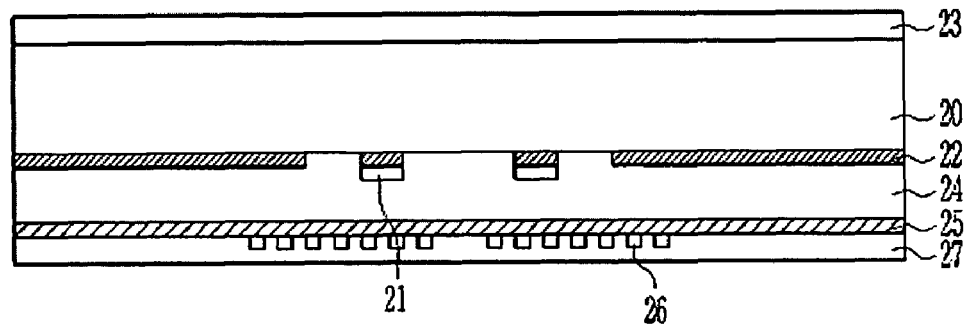

Referring to FIG. 3F, a detecting electrode pad 28 and a heater pad 29 can be open by a dry etching process to enable the electrical connection from the outside.

(Bulk Etching of a Semiconductor Substrate 22 and Forming a Substrate Dielectrics on Side of the Exposed Semiconductor Substrate)

Figure 3G:
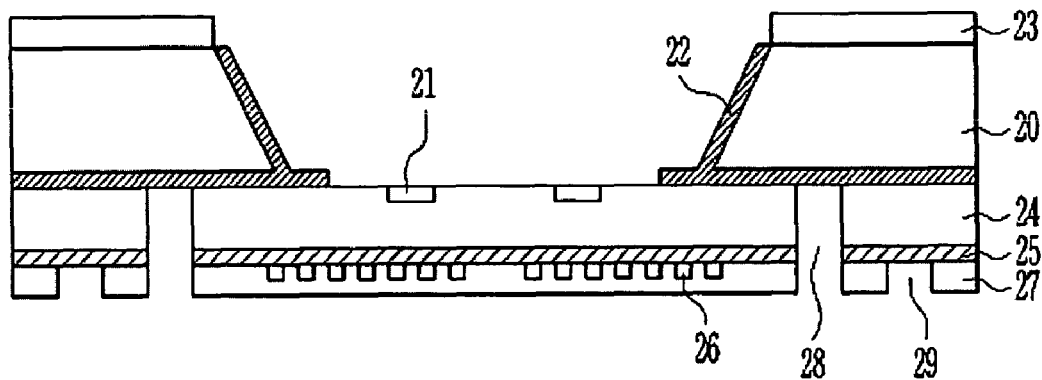

Referring to FIG. 3G, in order to minimize the heat loss and in order to form the well type structure that can contain the sensor solution, the semiconductor substrate 20 is bulk-etched in the side opposite to the side where the electrode is formed. When the silicon substrate is used, the silicon substrate can be anisotropically wet etched by using KOH or tri-methyl ammonium hydroxide (TMAH) as an etchant, for example. The well structure formed herein serves to prevent a sensor material dropped onto the electrode in the subsequent process from being diffused, and to make the sensor material reproducibly formed in the uniform thickness. Further, in the well structure having the membrane dielectric layer 24 and the supplementary dielectric layer 25, the substrate that corresponds to the well floor is totally removed, so that the heat loss is reduced when the heater heat line 26 heats the sensor material, allowing the microheater to operate in low power.

Due to the bulk etching of the semiconductor substrate 22, the lateral side of the semiconductor substrate is not protected with a substrate dielectric layer that protects the semiconductor substrate in the well structure, an thus is exposed to the outside, so that the substrate protective layer 22 is made formed by a hard mask process. The hard mask process is a process that selectively deposits a dielectric layer only on sidewall of the well structure, by making the hard mask where a portion corresponding to the sidewall of the well is pitted contact with another face of the mask, followed by depositing the dielectric layer. Preferably, the thin film is made of silicon oxide or aluminium oxide, and the like.

(Forming a Sensing Layer)

Next, a sensing layer that can react with the analyzed chemical species in the well structure to derive the change of the physical quantity should be formed. As a commonly used physical quantity, there is mass or electric conductivity derived from absorption of the chemical species.

As a sensor that detects chemical species in gas phase, there are QCM or SAW devices, and as a sensor that detects the electric conductivity, there exist devices using metal-oxide-semiconductor, conducting polymer and conductive particle-organic composite sensors. Among these sensors, it is desirable to fabricate a sensor array using the conductive particle-organic composite material that has an excellent stability against the external environment, and is appropriate to a very small electronic nose system with various non-specific sensors.

The conductive particle-organic composite sensor diffuses the electrical conductive particles into the non-conductive organic medium to have a restrained electrical conductive path, and uses a principal that the resistance of the composite varies when the analyzed chemical species is intruded into the sensor material. For example, as a conductive metal particle, there can be used nanoparticles comprising Au, Ag, Palladium, and Cu. As a conductive particle-organic composite sensor, there are a carbon black-polymer composite made of a conductive carbon black particle and a non-conductive polymer, and a organic-covered metal particle sensor comprising the metal particles protected by organic molecules on their surfaces.

A composite sensor fabricated with a carbon black particle and a non-conductive polymer will now be described. To form various chemical sensor combinations, a type of the non-conductive polymer can be changed, and characteristics of the non-conductive polymer can also be changed by using a mixed polymer where different polymers are mixed or by adding single molecule organic.

Typical non-conductive polymer materials are listed in Table 1, and as a typical additive, there are di(2-ethylhexyl) phthalate or dioctyl phthalate, and di(ethylene glycol) dibenzoate.

TABLE 1

| No | ID | Chemical name |
|---|---|---|
| 1 | PS | polystyrene |
| 2 | PMMA | poly(methly methacrylate) |
| 3 | PVP | polyvinylpyrrolidone |
| 4 | PVA | poly(vinyl acetate) |
| 5 | PEO | poly(ethlene oxide) |
| 6 | PMS | poly($\alpha$-methylstyrene) |
| 7 | PVPh | poly(4-vinylphenol) |
| 8 | PSF | polysulfone |
| 9 | PCL | polycaprolactone |
| 10 | P4MS | poly(4-methylstyrene) |
| 11 | PS-MMA | poly(stylene-co-methyl methacrylate) |
| 12 | PE-VA | poly(ethylene-co-vinyl acetate) |
| 13 | PVC-AN | poly(vinylidene chloride-co-acrylonitrile) |
| 14 | PS-AA | poly(stylene-co-allyl alcohol); Hydroxyl 5.8-7% |
| 15 | PMVE&MA | poly(methly vinyl ether-alt-maleic anhydride) |
| 16 | PS-BD | poly(styrene-co-butadiene); 45 wt % styrene |
| 17 | PBC | poly(Bisphenol A Carbonate) |
| 18 | PBD | poly(butadiene) |
| 19 | P4VP | poly(4-vinyl pyridine) |
| 20 | PS-MA | poly(styrene-co-maleic anhydride), 14% MA |
| 21 | PS-AN | poly(styrene-co-acrylonitrile); 25% AN |
| 22 | PE-AA | poly(ethylene-co-acrylic acid); 20% AA |
| 23 | PVC-VA | poly(vinyl chloride-co-vinyl acetate); 10% VA |
| 24 | PVB-VA-VA | poly(vinyl butyral)-co-vinyl alcohol-co-vinyl acetate; |
| 25 | PVS | poly(vinyl stearate); |
| 26 | EC | Ethyl cellulose |
| 27 | PS&IP&PS | polystyrene-black-polyisoprene-black-polystyrene); |
| 28 | HPC | hydroxypropyl cellulose |
| 29 | CA | cellulose acetate |
| 30 | PEG | poly(ethylene glycol) |

A process of forming a sensing layer will now be described in detail with reference to the conductive carbon black particle and the non-conductive polymer.

First, the non-conductive polymer is dissolved in a typical organic solvent. As a typical solvent, there are $CCl_4$, benzene, $CCl_2$, toluene, and ethyl alcohol. To effectively dissolve an insoluble polymer, it is heated up to about 50° C., and is stirred. A carbon black is put into the dissolved polymer solution, and shock is applied for 10 minutes to uniformly diffuse the carbon black particle into the solution. Typically, an amount of solvent used is 10 ml, the carbon is 20 mg, and the polymer is 80 mg.

The carbon black has a weight of 10% to 30% with respect to the overall sensor comprising the polymer and the carbon black, and preferably, the optimized sensor has a resistance of 10 k$\Omega$ to 10 M$\Omega$.

Meanwhile, in the case where the additive is used, and the sensor can be fabricated with a sum of weight of the polymer and the additive of 80 mg, and with the additive wt % in the range of 10 to 60%. As a method of forming the detecting layer using the composite solution prepared like this, there are a dispensing method that drops a drop into a detecting electrode using a micro pipette, a dipping method that dips a detecting electrode substrate into a solution and takes it back to make dry, and a spin coating that drops a solution into a detecting electrode and then rotates the substrate. In the case where an incorporated sensor array is used, the dispensing method that drops different solutions into the well structure is preferable.

As a method of fabricating another sensing layer, a solution that dissolves a gold nanoparticle where the surface is stabilized with —SH (thiol) group in a solvent such as toluene can be used to fabricate the sensing layer. Here, the fabrication methods presented above are used.

The fabricated chemical sensor array is mounted in a measurement chamber that can make the external gas sample to actively interact with the sensor material, using a part that controls the flow of the fluid and a flow path in which the fluid flows. Basically, in the gas sample chamber, a plate is attached onto the sensor array having a well structure to put the sensor material in the sealed space, and at one side, an inlet is arranged into which the fluid can flows, and at the other side, an outlet is arranged from which the fluid can flow out. It is preferable that the injected fluid sample interacts in the same condition as a number of detecting layers formed on the detecting electrode.

Figure 4:
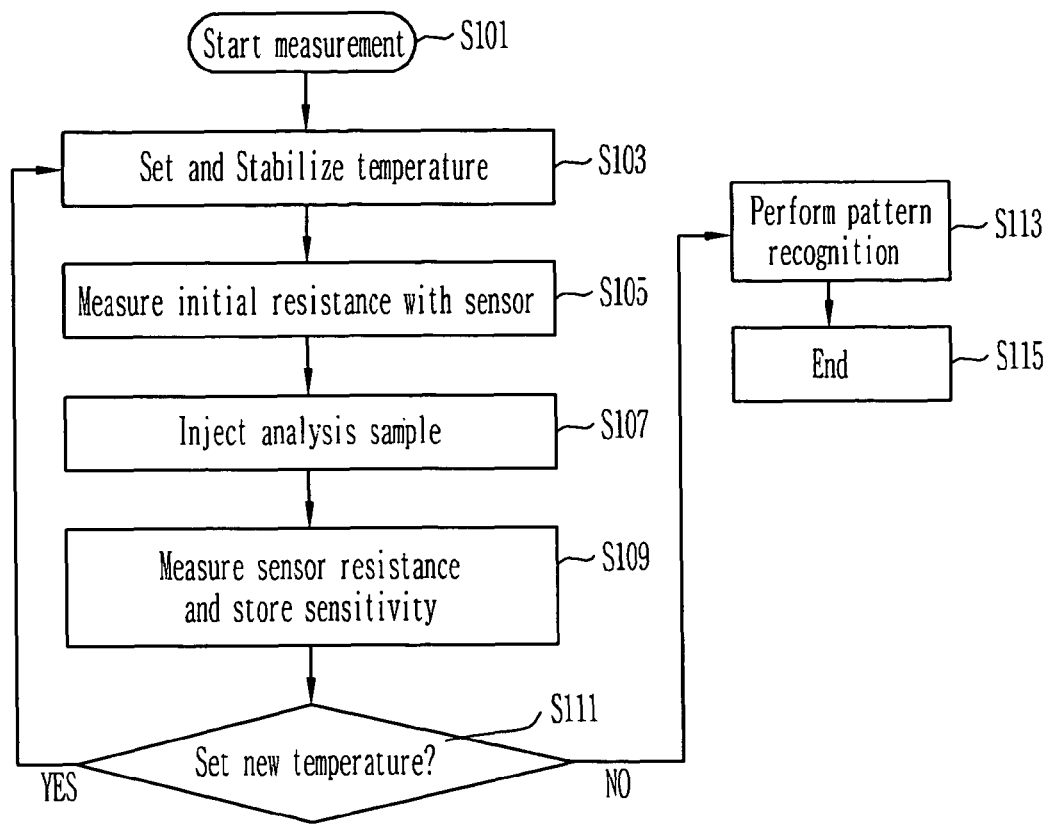
FIG. 4 is a flow chart illustrating how to determine chemical species and its concentration thereof with a measuring device on which a chemical sensor array is mounted according to an embodiment of the present invention.

FIG. 4 is a flow chart that illustrates a process of determining a chemical species and its concentration using a chamber equipped with the chemical sensor array according to an embodiment of the present invention.

When a measurement is started (S101), a temperature is set and stabilized in the state that dry air or nitrogen is flowed into the chamber (S103), and an initial resistance of a sensor is measured (S105). And then, a sample to be analyzed is injected (S107), and a resistance of the sensor is measured to store sensitivity (S109). Next, when there is a need to set a new temperature, it proceeds back to the step (S103) where a temperature is set again and stabilized, and when there is no need to set a new temperature, it proceeds to the step (S113) where the pattern recognition is performed.

Figure 5:
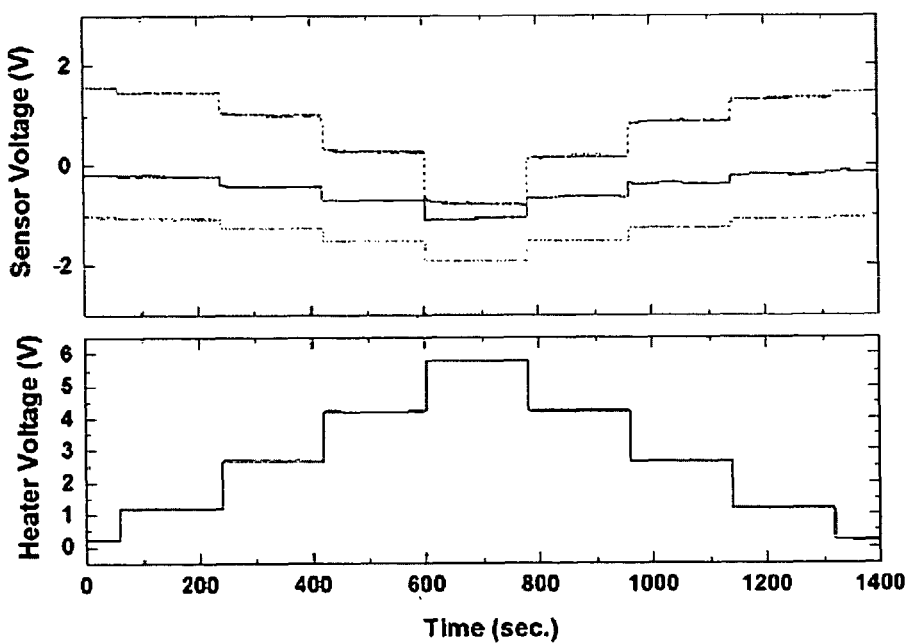
FIG. 5 is a plot showing a change with time for an initial resistance in a dry air state and for a voltage applied to both ends of a heater in order to control a temperature of the chemical sensor fabricated by the present invention.

FIG. 5 is a graph showing an initial resistance change of the sensor at the dry air state (upper portion) and a voltage applied across the heater (lower portion) in order to control the temperature of the chemical sensor fabricated in the present invention, along with time.

Referring to FIG. 5, stabilization over temperature of the sensor array is observed for more or less one second at the range of 20 to 60° C., and it takes several minutes to remove the pre-absorbed sample and to stabilize the initial resistance value. Therefore, power consumption can be reduced by stabilizing the initial resistance in the un-heated state followed by setting the temperature right before measurement.

Further, in order to stabilize the initial resistance in a short time, a sensor material is heated using a heater to facilitate desorption of the absorbed sample. After stabilized, the initial resistance is measured, and a resistance change after injecting the sample into the chamber is measured for a certain time. Using the initial and detecting resistance measured like this, the sensitivity for the detected sample is calculated and stored at each sensor. Generally, the detecting response is indicated as a percentage of the resistance that varies according to the initial resistance.

After the measurement for the specific set temperature is completed, when the measurement is required at another temperature, it is repetitively performed again from the initial stabilization step, and if all measurements are completed, the sample is analyzed through the pattern recognition algorithm using a sensitivity pattern measured at each temperature. When this analysis ends, all analyses are completed. When the pattern recognition is performed using the sensitivity pattern data measured at two or more temperatures, the sensitivity for each sensor at the specific temperature and the temperature-dependent change ratio of each sensor can be simultaneously used as parameters for performing the exact pattern recognition.

Figure 6:
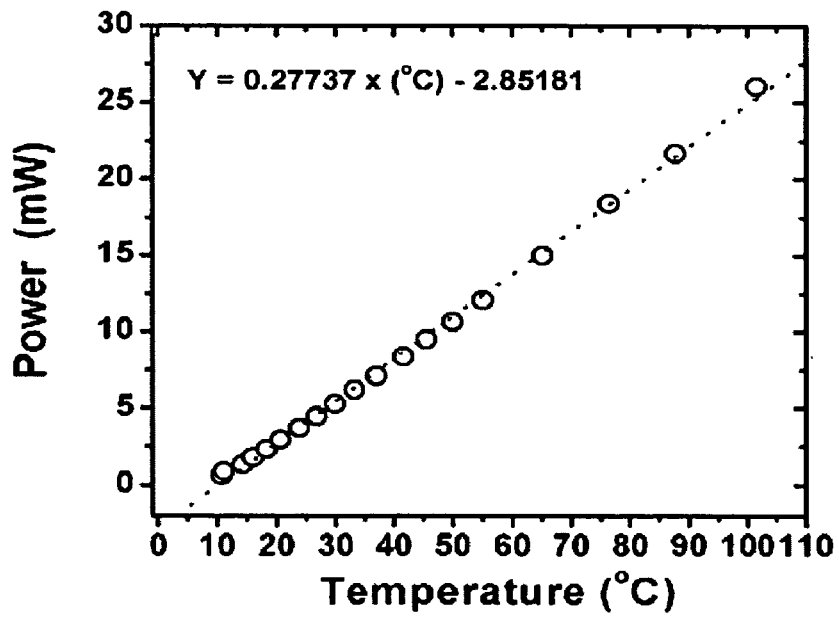
FIG. 6 is a graph showing the temperature to power consumption characteristics of a microheater included in the sensor structure of a sensor array according to an embodiment of the present invention.

FIG. 6 is a graph showing the temperature-power consumption characteristics of a microheater included in a sensor structure for use in fabricating a chemical sensor array according to an embodiment of the present invention. It shows power consumption related to a set temperature per unit sensor when the temperature is controlled with an incorporated heater for temperature control. If the temperature is set to the 40° C., about 7 mW power is consumed, which is far smaller than with the conventional sensor structure (Ref FIG. 1). Further, with the microheater, the temperature is set within several seconds, and the set temperature stabilization can be obtained, so that it can be appreciated that the operation of the heater is enabled almost during a measurement period. Generally, a time for measuring the sample while injecting it is about 10 to 250 seconds.

Experiment Example

In the experiment example, for each sensor of the sensor array, a carbon black-polymer composite was formed of insulating polymers comprising PEO (ethylene oxide), PEVA (ethylene-co-vinyl acetate, 40% vinyl acetate), PCL (caprolactone) and PMS (α-methylstyrene). Next, the polymer and the carbon black (ca. 15 wt %) were dissolved into chloroform. Next, the sensor film was fabricated with the Au electrode by spin coating on the glass substrate (50 nm thick electrode separated with 0.5 mm interval). Subsequently, four different analyte (methanol, ethanol, acetone, benzene) were sampled in the gas state, on the substrate arranged on the hot plate.

Figure 7:
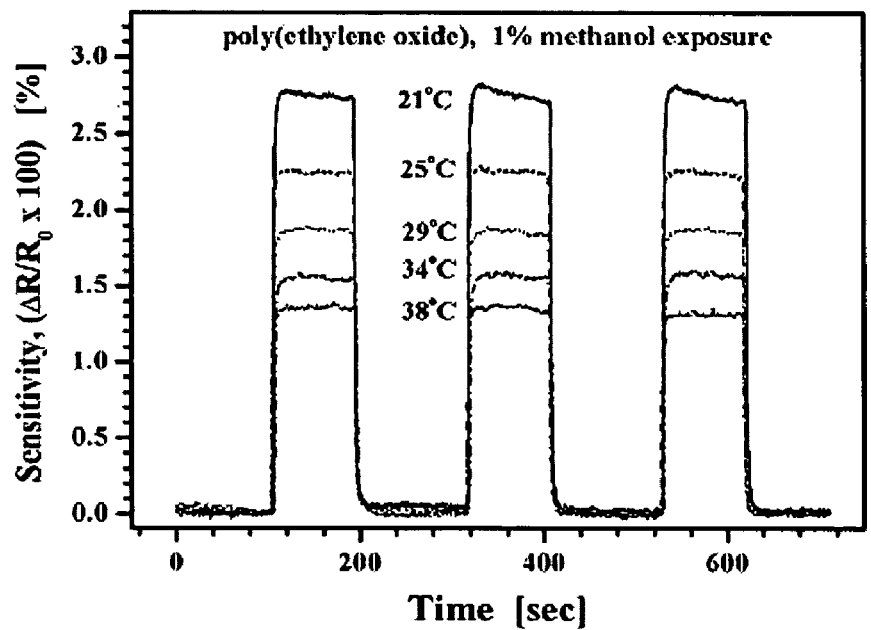
FIG. 7 is a diagram showing a typical time-dependent detecting response change in a sensor array according to an experiment of the present invention.

FIG. 7 shows a typical change in the detection response depending on the temperature in the sensor array according to the foregoing experiment example. It shows the measurement performed three times at one temperature and a resistance change versus time with a condition that the sample is injected for 100 seconds.

As a result, reproducibility is excellent, and as the temperature increases, it shows that the response tends to be decreased. The reason for such decrease of the detecting sensitivity is that a thermodynamic equilibrium between the sample and the sensor material moves in the decreasing direction of the amount of the sample within the sensor material. This thermodynamic shift follows a Van't Hoff plot, which is $d\{\ln S(i)\}/d(1/T) = -Ho/R$, where $S(i)$ indicates a detecting sensitivity, $Ho$ indicates a standard sample-sensor interactive enthalpy, $R$ indicates a gas constant, and $T$ indicates a sensor temperature.

Figure 8:
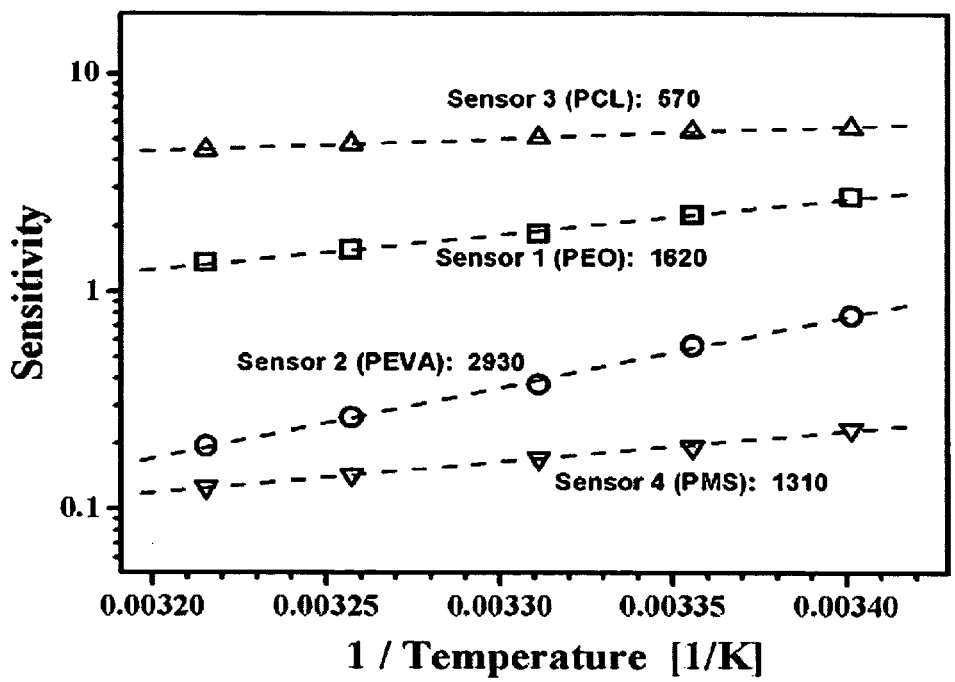
FIG. 8 is a schematic diagram showing a change between ln S(i) and 1/T to parameterize a time-dependent detecting response change in the sensor array according to the experiment of FIG. 7.

FIG. 8 is a schematic diagram showing a change between $\ln S(i)$ and $1/T$ in order to parameterize the detecting response change depending on the temperature in the sensor array according to the experiment example, and the number corresponding to the slope is found by a parameter obtained from the sensor response change to the temperature change. It can be noted that this parameter is determined as a different value according to the used composite sensor.

Figure 9:
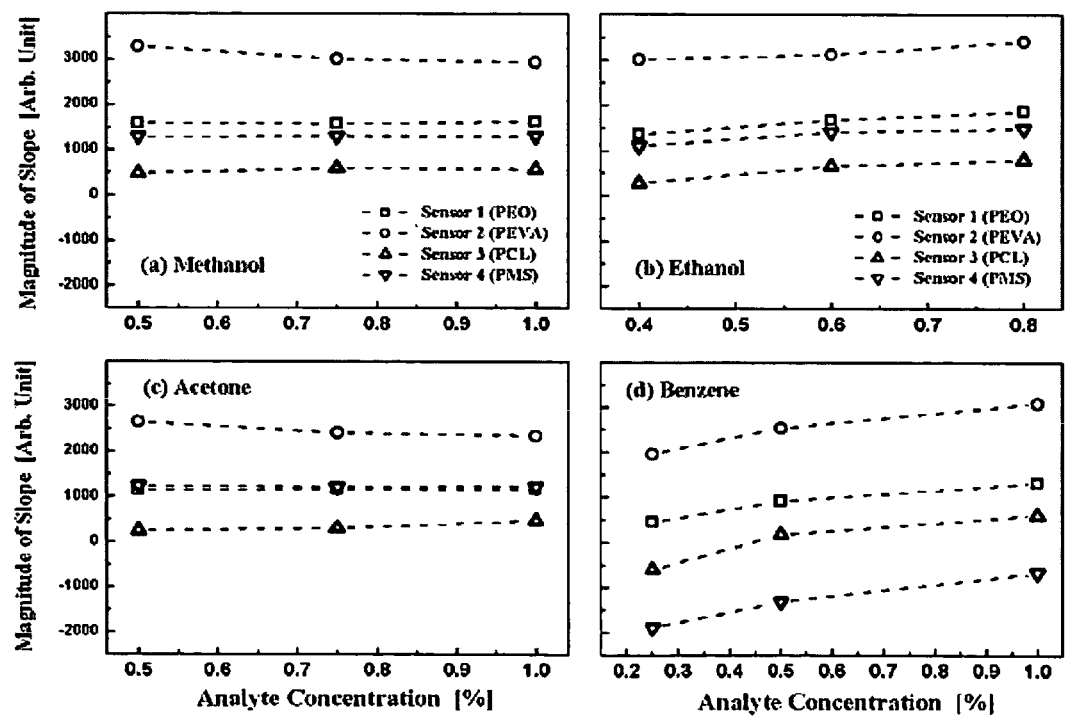
FIG. 9 is a graph showing a slope change of a Van't Hoff plot according to a concentration of the detected object chemical species in the experiment of FIG. 7.

FIG. 9 is a graph showing a slope change of the Van't Hoff plot based on the concentration of the detected object chemical species (methanol, ethanol, acetone, and benzene). The change of the parameter according to the various concentrations of the detecting samples of the methanol, ethanol, acetone, and benzene are shown herein. From this result, it is noted that a unique value is obtained for each sensor, while there is no significant change as to the concentration. It can be appreciated that since the slope found by the Van't Hoff plot is the thermodynamic enthalpy between the sample and the sensor accompanied by the detecting reaction, there is no significant change in this result with regard to the sample amount, it is mainly determined by the type of the sample and the sensor.

In the conventional method that determines the chemical species using the sensor array, it is determined through a pattern recognition algorithm using a parameter found by a physical quantity observed at the constant temperature, typically, the electrical conductivity.

However, according to the present invention, the heater, the detecting electrode and the detecting layer are formed on the membrane thin film to rapidly control the temperature, thereby having a merit that exact pattern recognition can be performed by deriving the parameter depending on the temperature change along with the physical quantity pattern at the specific temperature.

As a specific parameter for the temperature, there is a slope found by the Van't Hoff plot, which has an independent characteristic to the sample concentration allowing it to be usefully applied to the method of determining the chemical species and its concentration.

A variety of modifications can be made without departing from the spirit and scope of the present invention. Therefore, the description above with reference to the embodiments according to the present invention is provided for illustrative purpose only, and not for restricting the present invention, which is defined by the accompanying claims and their equivalents.

As described above, according to the present invention, a temperature of the sensor can be actively controlled by small power consumption, thereby implementing a constant temperature condition in the portable electronic nose system, and further, deriving a new parameter that determine a chemical species and its concentration through the measurement regarding the temperature change to allow the exact recognition for the analyzed object.

A method of analyzing the chemical species has advantages that a heat loss is reduced, and accordingly the power necessary to maintain the constant temperature is reduced, and a time required for a temperature change and stabilization is also reduced, compared with using the existing ceramic substrate.

Further, the parameter obtained from the temperature change is an indicator representing the interactive energy between the analyzed chemical species and the sensor material, which is independent to the concentration, thereby simultaneously determining the concentration and the chemical species when the recognition for the sensitivity, a parameter that is generally changed linearly to the concentration, together with the chemical species are performed.

What is claimed is:

1. A sensor structure comprising:
   a dielectric layer;
   a substrate formed on the dielectric layer and having a well structure exposing a surface of the dielectric layer;
   at least one pair of detecting electrodes embedded in the dielectric layer exposed by the well structure, wherein a surface of the detecting electrodes is in contact with the surface of the dielectric layer;
   an upper protective layer formed on an upper surface of the substrate;
   a substrate protective layer positioned and configured to at least cover a side wall of the well structure;
   a sensing layer formed on a detecting electrode and made of a conductive particle and a non-conductive polymer composite; and
   a heater embedded formed under the dielectric layer having the detecting electrodes for controlling a temperature in the well structure,
   wherein the detecting electrodes are directly between the heater and the planar surface at the bottom of the well structure, and
   wherein an analysis object is analyzed by measuring a change of a physical quantity of the sensing layers with regard to the exposure of a chemical species at two or more temperatures using the sensing layer.

2. The sensor structure according to claim 1, wherein detecting parameter patterns obtained from the measurement of the change of the physical quantity of the sensing layer with regard to the exposure of the chemical species of the analysis object are used to determine the chemical species and the concentration.

3. The sensor structure according to claim 2, wherein a detecting parameter of the detecting parameter patterns uses an electrical conductivity after and before the exposure of the chemical species.

4. The sensor structure according to claim 2, wherein a detecting parameter of the detecting parameter patterns uses the change of the electrical conductivity, and also uses a slope found through a Van't Hoff Plot of the detecting parameter obtained from the measurement of the electrical conductivity as a parameter with regard to the temperature change.

5. The sensor structure according to claim 1, wherein at least two sensor structures are arranged in an array form, the detecting parameter patterns obtained from the change of the physical quantity of the sensor array detecting layers are used with regard to the exposure of the chemical species of the analysis object to determine the chemical species and the concentration thereof.

6. The sensor structure according to claim 1, wherein the conductive particle includes at least one of carbon, gold, silver, palladium, and copper.

7. The sensor structure according to claim 1, wherein the non-conductive polymer is at least one of a single material and a compound thereof among materials in the following table:

| No | ID | Chemical name |
|---|---|---|
| 1 | PS | polystyrene |
| 2 | PMMA | poly(methly methacrylate) |
| 3 | PVP | polyvinylpyrrolidone |
| 4 | PVA | poly(vinyl acetate) |
| 5 | PEO | poly(ethlene oxide) |
| 6 | PMS | poly($\alpha$-methylstyrene) |
| 7 | PVPh | poly(4-vinylphenol) |
| 8 | PSF | polysulfone |
| 9 | PCL | polycaprolactone |
| 10 | P4MS | poly(4-methylstyrene) |
| 11 | PS-MMA | poly(stylene-co-methyl methacrylate) |
| 12 | PE-VA | poly(ethylene-co-vinyl acetate) |
| 13 | PVC-AN | poly(vinylidene chloride-co-acrylonitrile) |
| 14 | PS-AA | poly(stylene-co-allyl alcohol); Hydroxyl 5.8-7% |
| 15 | PMVE&MA | poly(methyl vinyl ether-alt-meleic anhydride) |
| 16 | PS-BD | poly(styrene-co-butadiene); 45 wt % styrene |
| 17 | PBC | poly(Bisphenol A Carbonate) |
| 18 | PBD | poly(butadiene) |
| 19 | P4VP | poly(4-vinyl pyridine) |
| 20 | PS-MA | poly(styrene-co-maleic anhydride), 14% MA |
| 21 | PS-AN | poly(styrene-co-acrylonitrile); 25% AN |
| 22 | PE-AA | poly(ethylene-co-acrylic acid); 20% AA |
| 23 | PVC-VA | poly(vinyl chloride-co-vinyl acetate); 10% VA |
| 24 | PVB-VA-VA | poly(vinyl butyral)-co-vinyl alcohol-co-vinyl acetate; |
| 25 | PVS | poly(vinyl stearate); |
| 26 | EC | Ethyl cellulose |
| 27 | PS&IP&PS | polystyrene-black-polyisoprene-black-polystyrene); |
| 28 | HPC | hydroxypropyl cellulose |
| 29 | CA | cellulose acetate |
| 30 | PEG | poly(ethylene glycol). |

8. The sensor structure according to claim 1, wherein the sensing layer further comprises any one of di(2-ethylhexyl) phthalate and di(ethylene glycol)dibenzoate as an additive.

9. The sensor structure according to claim 1, further comprising a film membrane disposed between the detecting electrodes and the heater configured to preclude electrical interference between the detecting electrodes and the heater.

10. The sensor structure according to claim 9, wherein the film membrane comprises a dielectric layer and a supplemental dielectric layer.

11. The sensor structure according to claim 10, wherein the dielectric layer is a 1.5 um silicon nitride layer and the supplemental layer is a 300 nm silicon oxide layer.

* * * * *